United States Patent
Knothe Tate et al.

(10) Patent No.: US 7,879,107 B2
(45) Date of Patent: Feb. 1, 2011

(54) COMPOSITION AND METHOD FOR INDUCING BONE GROWTH AND HEALING

(75) Inventors: Melissa L. Knothe Tate, Cleveland Heights, OH (US); Ulf R. Knothe, Cleveland Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1209 days.

(21) Appl. No.: 10/504,652

(22) PCT Filed: Feb. 20, 2003

(86) PCT No.: PCT/US03/04858

§ 371 (c)(1),
(2), (4) Date: Aug. 13, 2004

(87) PCT Pub. No.: WO03/070186

PCT Pub. Date: Aug. 28, 2003

(65) Prior Publication Data

US 2005/0107887 A1     May 19, 2005

Related U.S. Application Data

(60) Provisional application No. 60/358,160, filed on Feb. 20, 2002.

(51) Int. Cl.
    *A61F 2/28*     (2006.01)
(52) U.S. Cl. ............................... 623/23.61; 623/23.62
(58) Field of Classification Search .............. 623/23.48, 623/23.5, 23.51, 23.76, 23.61–23.63
    See application file for complete search history.

(56) References Cited

U.S. PATENT DOCUMENTS 4,141,864 A * 2/1979 Rijke et al. ................. 523/114
4,167,945 A   9/1979 Gottlieb (Continued)

FOREIGN PATENT DOCUMENTS

WO   PCT/GB81/00059     3/1981

(Continued)

OTHER PUBLICATIONS

Ajubi, N. E., et al., "Pulsating fluid flow increases prostaglandin production by cultured chicken osteocytes—a cytoskeleton-dependent process," *Biochem. Biophys. Res. Comm.*, vol. 25, pp. 62-68 (1996).

(Continued)

*Primary Examiner*—David H Willse
*Assistant Examiner*—Megan Wolf
(74) *Attorney, Agent, or Firm*—Pearne & Gordon LLP (57) ABSTRACT

A composition and method for inducing bone growth and healing is provided. The composition is useful for promoting new bone synthesis, and to enhance the mechanical stability and longevity of orthopaedic implants. The composition includes a bone endogenous material which is used as raw material for the body's natural osteogenic mechanism to synthesize new bone. The composition is applied in a flow phase and then undergoes a phase change to a congealed phase. The resulting material has a dual mode porosity system, having a first order porosity to accommodate and promote convective diffusion of nutrient species into and through the material, and a second order porosity to accommodate osteoblastic migration therein without the need for osteoclastic resorption.

65 Claims, 1 Drawing Sheet

U.S. PATENT DOCUMENTS

| | | | | |
|---|---|---|---|---|
| 4,645,503 A * | 2/1987 | Lin et al. | ................... | 623/23.58 |
| 4,882,149 A * | 11/1989 | Spector | ...................... | 424/425 |
| 5,475,052 A * | 12/1995 | Rhee et al. | ................. | 525/54.1 |
| 5,522,895 A * | 6/1996 | Mikos | ...................... | 623/23.58 |
| 5,683,249 A | 11/1997 | Ibsen et al. | | |
| 5,821,285 A * | 10/1998 | Khor et al. | ...................... | 524/27 |
| 5,935,594 A | 8/1999 | Ringeisen et al. | | |
| 6,077,916 A | 6/2000 | Laurencin et al. | | |
| 6,187,329 B1 * | 2/2001 | Agrawal et al. | .............. | 424/426 |
| 6,190,412 B1 * | 2/2001 | Lee et al. | ................. | 623/16.11 |
| 6,235,061 B1 * | 5/2001 | Laurencin et al. | ......... | 623/23.57 |
| 6,372,257 B1 * | 4/2002 | Marchosky | .................. | 424/488 |

FOREIGN PATENT DOCUMENTS

WO   PCT/US94/00413   1/1994

OTHER PUBLICATIONS

Ascenzi, A., et al., "An electron microscope study of osteon calcification," *Ultrastruct. Res.*, vol. 12, pp. 287-303 (1965).

Bergula, A. P., et al., "Femoral vein ligation increases bone mass in the hindlimb suspended rat," *Bone*, vol. 24, pp. 171-177 (1999).

Boyde, A., et al., "Scanning electron microscope studies of bone," *The Biochemistry and Physiology of Bone*, p. 290 (1992).

Canas, F., et. al., "Potassium and milieu interieur of bone," *Am. J. Physiol.*, vol. 217, pp. 1963-2120 (1969).

Carter, D. R., et al., "Mechanical loading history and skeletal biology," *J. Biomechanics*, vol. 20, pp. 1095-1109 (1987).

Chakkalakal, D. A., "Mechanoelectric transduction in bone," *J. Mater. Ros.*, vol. 4, pp. 1034-1046 (1989).

Civitelli, R., "Cell-cell communication in bone," *Calcif. Tissue Int.*, vol. 56, pp. S29-S31 (1995).

Currey, J. D., "Some effects of ageing in human Haversian systems," *J. Anat.*, vol. 98, pp. 69-75 (1964).

Dodd, J. S., et al., "Osteocyte hypoxia; a novel mechanotransduction pathway," *Am. J. Physiol.*, vol. 277 (3 Pt 1), pp. C598-602 (1999).

Gatzka, C., et al., "A novel ex vivo model for investigation of fluid displacements in bone after endoprosthesis implantation," *J. Mat. Sci: Mat. in Med.*, vol. 10, pp. 801-806 (1999).

Goodship, A. E., et al., "Functional adaptation of bone to increased stress," *J. Bone Jr. Surg.*, vol. 61A, pp. 539-546 (1979).

Greenwald, A. S., et al., "A pathway for nutrients from the medullary cavity to the articular cartilage of the human femoral head," *J Bone Jt Surg.*, vol. 51B, pp. 747-753 (1969).

Gross, D., et al., "Streaming potential and the electromechanical response of physiologically moist bone," *J. Biomechanics*, vol. 15, pp. 277-295.

Gross, P. M., et al., "Measurement of blood flow to bone and marrow in experimental animals by means of the microsphere technique," *J. Bone Joint Surg.*, vol. 63A, pp. 1028-1031 (1981).

Guzeisu, N., "Streaming potential of intact wet bone," *J. Biomechanics*, vol. 23, pp. 673-685 (1990).

Guzelsu, N., "The origin of electrokinetic potentials in bone tissue: the organic phase," *J. Biomechanics*, vol. 23, pp. 661-672 (1990).

Handagama, P. J., "Incorporation of intravenously injected albumin, immunoglobulin G and fibrinogen in guinea pig megakaryocyte granules," *J. Clin. Invest.*, vol. 84, pp. 73-82 (1989).

Hillsley, M. V., "Osteoblast hydraulic conductivity is regulated by calcitonin and parathyroid hormone," *J. Bone Min .Res.*; vol. 11, pp. 114-124 (1996).

Holmes, J. M., et al., "Gas adsorption and surface structure of bone mineral," *Biochemistry 3*, pp. 2019-2024 (1964).

Hui, P. W., et al., "Fluid conductance of cancellous bone graft as a predictor for graft-host interface healing," *J. Biomechanics*, vol. 29, pp. 123-132 (1996).

Hung, C. T., et al., "What is the role of the convective current density in the real-time calcium response of cultured bone cells to fluid flow?," *J. Biomechanics*, vol. 29, pp. 1403-1409 (1996).

Hung C. T., et al., "Intracellular $Ca^{2+}$ stores and Extracellular $Ca^{2+}$ are required in the real-time $Ca^{2+}$ response of bone cells experiencing fluid flow," *J. Biomechanics*, vol. 29, pp. 1411-1417 (1996).

Jacobs, C. R., et al., "Differential effect of steady versus oscillating flow on bone cells," *J. Biomechanics*, vol. 31, pp. 969-976 (1998).

Johnson, D. L., et al., "Fluid flow stimulates rapid and continuous release of nitric oxide in osteoblasts," *Am. J. Physiol.*, vol. 271, pp. E205-E208 (1996).

Johnson, M. W., et al., "Comparison of the electromechanical effects in wet and dry bone," *J. Biomechanics*, vol. 13, pp. 437-442 (1980).

Johnson, M. W., et al., "Fluid flow in bone in vitro," *J. Biomechanics*, vol. 15, pp. 881-885 (1982).

Karnovsky, M. J., "The ultrastructural basis of capillary permeability studied with peroxidase as a tracer," *J. Cell Biology*, vol. 35, pp. 213-236 (1967).

Kelly, P. J., et al., "Venous pressure and bone formation," *Microvascular Research*, vol. 39, p. 364 (1990).

Klein-Nulend, J.,et al., "Pulsating fluid flow increases nitric oxide (NO) synthesis by osteocytes but not periosteal fibroblasts-correlation with prostaglandin upregulation," *Biochem. and Biophys. Res. Comm.*, vol. 217, pp. 640-647 (1995).

Knothe Tate M. L., "Interstitial Fluid Flow," *Bone Biomechanics Handbook*, Ch. 22, pp. 1-29 (2001).

Knothe Tate, M. L., et al., "In vivo demonstration of load-induced fluid flow in the rat tibia and its potential implications for processes associated with functional adaptation," *J. Exp. Biol.*, vol. 203, pp. 2737-2745 (2000).

Knothe Tate, M. L., et al., "An ex vivo model to study transport processes and fluid flow in loaded bone," *J. Biomechanics*, vol. 33, pp. 247-254 (2000).

Knothe Tate, M. et al., "A theoretical FE-based model developed to predict the relative contribution of convective and diffusive transport mechanisms for the maintenance of local equilibria within cortical bone," *Advances in Heal and Mass Transfer in Biotechnology*, HTD-vol. 362/BED- vol. 40, pp. 133-142 (1998).

Kufahl, R. H., et al., "A theoretical model for stress-generated fluid flow in the canaliculi-lacunae network in bone tissue," *J. Biomechanics*, vol. 23, pp. 171-180 (1990).

Lang, S., Stipanich, N., et al., "Diffusion of glucose in stressed and unstressed canine femur in vitro," *Annals of the New York Academy of Sciences*, vol. 238, pp. 139-148 (1974).

Lanyon, L. E., et al., "Strain related electrical potentials recorded in vitro and in vivo," *Calcit. Tiss. Res.*, vol. 22, pp. 315-327 (1977).

Li, G. P., et al., "Permeability of cortical bone of canine tibiae," *Microvasc. Res.*, vol. 34, pp. 302-310 (1987).

Luo, G., et al., "Implementation of strain rate as a bone remodeling stimulus," *J. Biomech. Eng.*, vol. 117, pp. 329-338 (1995).

Mak A.F., et al., "Deformation-induced hierarchical flows and drag forces in bone canaliculi and matrix microporosity," *J. Biomech.*, vol. 30, pp. 11-18 (1997).

McCarthy, I. D., "Clearance of albumin by cortical bone and marrow," *Clin. Orth. and Rel. Res.*, vol. 334, pp. 24-29 (1997).

McCarthy, I. D., et al., "A distributed model of exchange processes within the osteon," *J. Biomechanics*, vol. 25, pp. 441-450 (1992).

Menton D. N., et al., "From bone lining cell to osteocyte—an SEM study," *Anatomical Record* vol. 209, pp. 29-39 (1984).

Morris, M. A., et al., "Fluid spaces in canine bone and marrow," *Microvasc. Res.*, vol. 23, pp. 188-200 (1982).

Nachemson, A., et al., "In vitro diffusion of dye through the end plates and annulus fibrosis of human lumbar intervertebral discs," *Acto. orthopscand.*, vol. 41, pp. 589-607 (1970).

Neuman, M. W., et al., "On the measurement of water compartments, pH and gradients in calvaria," *Calcif. Tiss. Int.*, vol. 31, pp. 135-145 (1980).

Otter, M., et al., "Evidence for different sources of stress-generated potentials in wet and dry bone," *J. Orth. Res.*, vol. 3, pp. 321-324 (1985).

Otter, M., et al., "Streaming potentials in chemically modified bone," *J. Orth. Res.*, vol. 6, pp. 346-359 (1988).

Owen, M., et al., "Extravascular albumin in bone tissue," *J. Physiol.*, vol. 257, pp. 293-307 (1976).

Petrov, N., et al., "A discrete model for straming potentials in a single osteon," *J. Biomechanics*, vol. 22, p. 517-521 (1989).

Pollack, S., et al., "An anatomical model for streaming potentials in osteons," *J. Biomechanics*, vol. 17, pp. 627-636 (at least as early as Feb. 19, 2001).

Salzstein, R. A., et al., "Electromechanical potentials in cortical bone—I. A continuum approach," *J. Biomechanics*, vol. 20, pp. 261-270 (1987).

Salzstein, R. A., et al., "Electromechanical potentials in cortical bone—II. Experimental analysis," *J. Biomechanics*, vol. 20, pp. 271-280 (1987).

Smalt R., et al., "Induction of NO and prostagiandin E2 in osteoblasts by wall-shear stress but not mechanical strain," *Am. J. Physiol*, vol. 273, pp. E751-E758 (1997).

Steck R., et al., "A Finite Difference model of load induced fluid displacements within bone under mechanical loading," *Medical Engineering & Physics*., vol. 22(2), pp. 117-125 (2000).

Timmins, P. A., et al., "Bone water," *Calc. Tissue Res*., vol. 23, pp. 1-5 (at least as early as Feb. 19, 2001).

Turner, C. H., et al.; "Mechanotransduction in bone: Do bone cells act as sensors of fluid flow?," *FASEB*, vol. 8, pp. 875-878 (1994).

Weinbaum, S., et al., "A model for the excitation of osteocytes by mechanical loading induced bone shear stresses," *J. Biomechanics*, vol. 27, pp. 339-360 (1994).

You, J., et al., "Substrate deformation levels associated with routine physical activity are less stimulatory to bone cells relative to loading-induced oscillatory fluid flow," *J. Biomech Eng*., vol. 122, pp. 387-393 (2000).

M. L. Knothe Tate, et al., "In Vivo Tracer Transport Through the Lacunocanalicular System of Rat Bone in an Environment Devoid of Mechanical Loading," *Bone*, vol. 22, No. 2, pp. 107-117 (1998).

G. Marotti, et al., "Quantitative Investigation on Osteocyte Canaliculi in Human Compact and Spongy Bone," *Bone*, vol. 6, pp. 335-337 (1985).

R. B. Martin, "Toward a Unifying Theory of Bone Remodeling," *Bone*, vol. 26, No. 1, pp. 1-6 (2000).

Elisabeth M. Aarden, et al., "Function of Osteocytes in Bone," *Journal of Cellular Biochemistry*, vol. 55, pp. 287-299 (1994).

Charles A. Baud, M.D., et al., "Submicroscopic Structure and Functional Aspects of the Osteocyte," *Clinical Orthopaedics and Related Research*, No. 56, pp. 227-236 (1968).

Elisabeth H. Burger, et al., "Mechanotransduction in bone—role of the lacunocanalicular network," *The FASEB Journal*, vol. 13, pp. S101-S112 (1999).

D. B. Burr, et al., "The Effects of Altered Strain Environments on Bone Tissue Kinetics," *Bone*, vol. 10, pp. 215-221 (1989).

David A. Bushinsky, et al., "Ion microprobe analysis of mouse calvariae in vitro: evidence for a "bone membrane"," *The American Physiological Society*, pp. E152-E158 (1989).

S. C. Cowin, et al., "A Case For Bone Canaliculi as the Anatomical Site of Strain Generated Potentials," *J. Biomechanics*, vol. 28, No. 11, pp. 1281-1297 (1995).

Todd A. Curtis, et al., "Canalicular Communication in the Cortices of Human Long Bones," *The Anatomical Record*, vol. 212, pp. 336-344 (1985).

Peter P. H. De Bruyn, et al., "In-vivo endocytosis by bristle-coated pits and intracellular transport of endogenous albumin in the endothelium of the sinuses fo liver and bone marrow," *Cell. Tissue Res*., vol. 240, pp. 1-7 (1985).

Richard M. Dillaman, et al., "Fluid Movement in Bone: Theoretical and Empirical," *J. Biomechanics*, vol. 24, Suppl. 1, pp. 163-177 (1991).

H. J. Donahue, et al., "Gap Junctions and Biophysical Regulation of Bone Cell Differentiation," *Bone*, vol. 26, No. 5, pp. 417-422 (2000).

Stephen B. Doty, "Morphological Evidence of Gap Junctions Between Bone Cells," *Calcif. Tissue Int*., vol. 33, pp. 509-512 (1981).

R. L. Duncan, et al., "Mechanotransduction and the Functional Response of Bone to Mechanical Strain," *Calcif. Tissue Int*., vol. 57, pp. 344-358 (1995).

M. R. Forwood, et al., "The Response of Rat Tibiae to Incremental Bouts of Mechanical Loading: A Quantum Concept for Bone Formation," *Bone*, vol. 15, No. 6, pp. 603-609 (1994).

M. R. Forwood, et al., "Skeletal Adaptations to Mechanical Usage: Results From Tibial Loading Studies in Rats," *Bone*, vol. 17, No. 4, pp. 197S-205S (1995).

Harold M. Frost M.D., et al., "The Pathomechanics of Osteoporoses," *Pathomechanics of Osteoporoses*, No. 200, pp. 198-225 (1985).

Ted S. Gross, et al., "Physiological and Genomic Consequences of Intermittent Hypoxia Selected Contribution: Osteocytes upregulate HIF-1 in response to acute disuse and oxygen deprivation," *J. Appl. Physiol*., vol. 90, pp. 2514-2519 (2001).

Mark A. Haidekker, et al., "Fluid shear stress increases membrane fluidity in endothelial cells: a study with DCVJ fluorescence," *Am. J. Physiol. Heart Circ. Physiol*., vol. 278, pp. H1401-H1406 (2000).

L. V. Harter, et al., "Human Osteoblast-Like Cells Respond to Mechanical Strain with Increased Bone Matrix protein Production Independent of Hormonal Regulation," *Endocrinology*, vol. 136, No. 2, pp. 528-535 (1995).

Sean Hughes, et al., "Fluid Space in Bone," *Clinical Orthopaedics and Related Research*, No. 134, pp. 332-341 (1978).

Marvin W. Johnson, "Behavior of Fluid in Stressed Bone and Cellular Stimulation," *Calcif. Tissue Int*., vol. 36, pp. S72-S76 (1984).

L. Carlos Junqueira, M.D., et al., "Bone," *1989 Basic Histology*, Sixth Edition, pp. 136-159 (1989).

Russell G. Keanini, et al., "A Theoretical Model of Circulatory Interstitial Fluid Flow and Species Transport Within Porous Cortical Bone," *J. Biomechanics*, vol. 28, No. 8, pp. 901-914 (1995).

Gregory J. King, et al., "Actin-Like Filaments in Bone Cells of Cultured Mouse Calvaria as Demonstrated by Binding to Heavy Meromyosin," *The Journal of Cell Biology*, vol. 66, pp. 445-451 (1975).

W. A. McDougall, "Pathways of Penetration and Effects of Horseradish Peroxidase in Rat Molar Gingiva," *Archs. oral Biol*., vol. 15, pp. 621-633 (1970).

Ronald J. Midura, et al., "Parathyroid Hormone Stimulates Hyaluronan Synthesis in an Osteoblast-like Cell Line," *The Journal of Biological Chemistry*, vol. 269, No. 18, pp. 13200-13206 (1994).

Kenneth J. Noonan, et al., "Spatial Distribution of CD44 and Hyaluronan in the Proximal Tibia of the Growing Rat," *Journal of Orthopaedic Research*, vol. 14, No. 4, pp. 573-581 (1996).

M. W. Otter, et al., "Transcortical Streaming Potentials Are Generated by Circulatory Pressure Gradients in Living Canine Tibia," *J. Orthop. Res*., vol. 8, No. 1 (1990).

Mark W. Otter, et al., "A Comparative Analysis of Steaming Potentials In Vivo and In Vitro," *J. Orthop. Res*., vol. 10, pp. 710-719 (1992).

Roy V. Talmage, Ph.D., "Calcium Homeostasis—Calcium Transport—Parathyroid Action," *Clinical Orthopaedics and Related Research*, No. 67, pp. 210-225 (1969).

K. Piekarski, "Fracture of Bone," *Journal of Applied Physics*, vol. 41, No. 1, pp. 215-223 (1970).

K. Piekarski, "Analysis of Bone as a Composite Material," *Int. J. Engng. Sci*., vol. 11, pp. 557-565 (1973).

K. Piekarski, et al., "Transport mechanism operating between blood supply an dosteocytes in long bones," *Nature*, vol. 269, No. 1, pp. 80-82 (1977).

Gwendolen C. Reilly, et al., "Investigation of the Morphology of the lacunocanalicular System of Cortical Bone Using Atomic Force Microscopy," *Annals of Biomedical Engineering*, vol. 29, pp. 1074-1081 (2001).

Robert A. Robinson, M. D., "Observations Regarding compartments for Tracer Calcium in the Body," *Bone Mineral Dynamics*, Chapter 23, pp. 423-439 (at least as early as Feb. 19, 2001).

E. H. Starling, "On the Absorption of Fluids From the Connective Tissue Spaces," *Absorption by Blood Vessels*, pp. 313-326 (at least as early as Feb. 19, 2001).

C. J. Vander Wiel, Ph.D., et al., "The Presence of lining Cells on Surfaces of Human Trabecular Bone," *Lining Cells on Human Trabecular Bone*, No. 134, pp. 350-355 (1978).

N. Vongsavan, et al., "Fluid Flow Through Cat Dentine In Vivo," *Archs. Oral. Biol*., vol. 37, No. 3, pp. 175-185 (1992).

Liyun Wang, et al., "Fluid pressure relaxation depends upon osteonal microstructure: modeling an oscillatory bending experiment," *Journal of Biomechanics*, vol. 32, pp. 663-672 (1999).

Ning Wang, et al., "Mechanotransductin Across the Cell Surface and Through the Cytoskeleton," *Science*, vol. 260, No. 5111, pp. 1124-1127 (1993).

Kaut Aukland, "Distribution of body fluids: local mechanisms guarding interstitial fluid volume," *J. Physiol*, vol. 79, pp. 395-400 (1984).

G. Baltadzhiev, "Morphology of the Haversian Canal," *Folia Medica*, vol. XXXVI, No. 1, pp. 21-28 (1994).

Eiichi Fukada, et al., "On the Piezoelectric Effect of Bone," *Journal of the Physical Society of Japan*, vol. 12, No. 10, pp. 1158-1162 (1957).

R. B. Johnson, et al., "A Re-examination of the Osteocytic Network of Interdental Bone," *J. Submicrosc. Cytol.*, vol. 15, No. 3, pp. 619-625 (1983).

G. Marotti, et al., "Structure-function relationships in the osteocyte," *Italian Journal of Mineral & Electrolyte Metabolism*, vol. 4, No. 2, pp. 93-106 (1990).

Alice Maroudas, "Physicochemical Properties of Cartilage in the Light of Ion Exchange Theory," *Biophysical Journal*, vol. 8, pp. 575-595 (1968).

Scott C. Miller, et al., "Bone Lining Cells: Structure and Function," *Scanning Microscopy*, vol. 3, No. 3, pp. 953-961 (1989).

R. Steck, et al., "Prediction of Load-induced Fluid Flow in Bone and its Implications for Transport Phenomena," pp. 755-760 (at least as early as Feb. 19, 2001).

F. Wassermann, et al., "Fine Structure of the osteocyte Capsule and of the Wall of the Lacunae in Bone," *Z. Zeilforsch.*, vol. 67, pp. 636-652 (1965).

Ephraim Weinstein, D.D.S., et al., "Studies of Gingival Fluid," *Periodontics*, vol. 5, No. 4, pp. 161-166 (1967).

S. M. Willans, et al., "Distributed Model of Blood-bone Exchange," pp. 1-9 (1985).

Julius Wolff, "*The Law of Bone Remodelling*," pp. 1-67, *Springer-Verlag*, (1892).

S. R. Pollack, et al., "An Anatomical Model for Streaming Potentials in Osteons," *J. Biomechanics*, vol. 17, No. 8, pp. 627-636 (1984).

Sanjay Mishra, et al., "Effect of Lacunocanalicular Architecture on Hydraulic Conductance in Bone Tissue: Implications for Bone Health and Evolution," *The Anatomical Record, Part A*, vol. 273A, pp. 752-762 (2003).

Charles H. Turner, et al., "Mechanotransduction in bone: role of strain rate," *The American Physiological Society*, pp. E438-E442 (1995).

Melissa L. Knothe Tate, et al., "Experimental Elucidation of Mechanical Load-Induced Fluid Flow and Its Potential Role in Bone Metabolism and Functional Adaptation," *The American Journal of the Medical Sciences*, pp. 189-195 (1998).

P. J. Atkinson, et al., "The spatial structure of bone," pp. 179-199 (at least as early as Feb. 19, 2001).

E. H. Burger, et al., "Influence of Mechanical Factors on Bone Formation, Resorption and Growth In Vitro," Chapter 2, pp. 37-56 (1993).

William G. Seliger, "Tissue Fluid Movement in Compact Bone," *Anat. Rec.*, vol. 166, pp. 247-256 (at least as early as Feb. 19, 2001).

E. M. Landis, et al., "Exchange of substances through the capillary walls," *Handbook of Physiology*, Circulation II, pp. 961-1034 (at least as early as Feb. 19, 2001).

Maya Simionescu, et al., "Ultrastructure of the microvascular wall: functional correlartions," Handbook of Physiology, The Cardiovascular System IV, pp. 41-101 (at least as early as Feb. 19, 2001).

Francois Berthiaume, "Tissue Engineering, Effects of Fluid Flow on Cells," *Science & Medicine*, pp. 6-7 (2000).

Reginald R. Cooper, et al., "Morphology of the Osteon," *The Journal of Bone and Joint Surgery*, vol. 48-A, No. 7, pp. 1239-1271 (1966).

S. C. Cowin, et al., "Candidates for the Mechanosensory System in Bone," *Journal of Biomechanical Engineering*, vol. 113, pp. 191-197 (1991).

Rik Huiskes, et al., "From Structure to Process, From Organ to Cell: Recent Developments of FE-Analysis in Orthopaedic Biomechanics," *Transactions of the ASME*, vol. 115, pp. 520-527 (1993).

Richard J. Montgomery, et al., "Interstitial Fluid Flow in Cortical Bone," *Microvascular Research*, vol. 35, pp. 295-307 (1988).

Jan Z. Geisler, et al., "The Membrane Control of Bone Potassium," pp. 608-612 (at least as early as Feb. 19, 2001).

C. Eriksson, "Streaming Potentials and Other Water-Dependent Effects in Mineralized Tissues," *Annals New York Academy of Sciences*, pp. 321-338 (at least as early as Feb. 19, 2001).

J. S. Arnold, et al., "The Osteocyte as a Water Pump," *Clinical Orthopaedics*, vol. 78, pp. 47-55 (1971) (edited and expanded version of paper).

I.D. McCarthy, M.D., "Clearance of albumin by cortical Bone and Marrow," *Clin Orthop*, vol. 334, pp. 24-29 (1997).

A. E. Tami, et al., "Probing the tissue to subcellular level structure underlying bone's molecular sieving function," Biorheology, vol. 40, pp. 577-590 (2003).

Melissa L. Knothe Tate, ' "Whiter flows the fluid in bone?,'" *Journal of Biomechanics*, vol. 36, pp. 1409-1424 (2003).

Marijke E. Holtrop, et al., "Ultrastructural Evidence for a Transport System in Bone," pp. 365-374 (at least as early as Feb. 19, 2001).

J. K. Gladden, et al., "Diffusion in Supersaturated Solutions. II. Glucose Solutions," vol. 75, pp. 3900-3904 (1952).

\* cited by examiner

Fig. 1

COMPOSITION AND METHOD FOR INDUCING BONE GROWTH AND HEALING

This application claims the benefit of U.S. Provisional Patent Application Ser. No. 60/358,160 filed Feb. 20, 2002, which is hereby incorporated by reference in its entirety.

The invention relates to a composition that induces bone growth and healing. More particularly, it relates to a composition that facilitates rapid bone healing and adhesion to a non-cemented endoprosthetic implant. Such a composition preferably facilitates osteoconduction toward a non-cemented endoprosthetic implant by enhanced molecular transport and cellular mechanical loading via load-induced fluid flow to promote implant stability and longevity.

BACKGROUND OF THE INVENTION

It is often necessary to implant an endoprosthetic device within the living bone of a patient, e.g. during a hip replacement surgery. In this procedure, the medullary canal within the bone is first reamed as known in the art, and then an endoprosthesis having a long shaft is thrust into the reamed canal to form an interference fit therein.

Unfortunately, this interference fit method of endoprosthetic implantation often results in a poor fit between the prosthesis and surrounding bone tissue, resulting in a gap at the interface between the bone and the prosthesis. What starts as micromotion, typically in the proximal area of the implant, can result in instability of the implant over time. As the implant becomes looser and more unstable within the medullary canal, it moves increasingly back and forth from cyclic loading within the medullary canal, grinding against the surrounding bone tissue. This can result in both mechanical wear and osteoclastic resorption of surrounding bone tissue, further compounding endoprosthetic instability. The short-term result is enhanced pain for the patient, and the ultimate result is a failure of the endoprosthetic implant which must be replaced surgically. However, surgical replacement becomes more difficult with each failure because the prior reaming of the medullary canal and loosening of the implant through osteoclastic resorption greatly reduce the amount and quality of available bone tissue to anchor the implant.

In addition, endoprosthetic implantation has traditionally been limited largely to the elderly population. Therefore, in the past, endoprostheses were not usually required or expected to have useful lives longer than about 10-15 years. However, it is becoming more common to implant endoprostheses in younger patients, for example in young adults 18-50 years of age. It is desirable, especially for younger patients, that endoprostheses have a useful lifespan longer than the traditional 10-15 years, preferably at least 20, 25, or 30 years, or longer. Accordingly, there is a need in the art for a material to fill the gap between an endoprosthetic implant and the surrounding bone tissue in the medullary canal that provides a longer useful life for the implant. Such a material preferably will speed healing of bone tissue in the medullary canal following implantation, and most preferably it will promote bone growth and adhesion toward (preferably to) the implant itself.

SUMMARY OF THE INVENTION

A composition is provided having a bone endogenous material and a degradable polymer material. The degradable polymer material has a half-life for degradation of 1-30 days.

A method of promoting osteogenesis is also provided including the steps of: a) providing a composition having a bone endogenous material in a flow phase; b) applying the composition to a site within a patient where it is desired to synthesize new bone; c) the composition undergoes a phase transformation from the flow phase to a congealed phase; and d) providing a dual mode porosity system in the composition in its congealed phase, wherein the congealed phase of the composition has a first order porosity and a second order porosity.

A compliant barrier layer in an intra-medullary gap between a medullary canal wall of a bone and an endoprosthesis implanted within the medullary canal is also provided. The compliant barrier layer includes a bone endogenous material, and has a dual mode porosity system with a first order porosity and a second order porosity. The said second order has a larger mean Stokes diameter than the first order porosity.

DETAILED DESCRIPTION OF THE PREFERRED EMBODIMENTS OF THE INVENTION

As used herein, when a preferred range is given, such as 5-25 (or 5 to 25), this means preferably at least 5 and, separately and independently, preferably not more than 25.

The invention comprises a composition that is effective to induce bone healing and bone growth, as well as to enhance the mechanical stability and longevity of orthopaedic implants. This composition is referred to as "bone prime" herein because in a preferred embodiment it is used to prepare or 'prime' the reamed medullary canal within a long bone to receive and accommodate an endoprosthetic shaft therein. The composition provides a semi-rigid, compliant barrier layer in the annulus or annular gap between the endoprosthetic shaft and the medullary canal wall, which barrier layer promotes osteoconduction and bone growth from the bone toward (and to) the prosthesis as will be described. The bone primer can be provided within the medullary canal prior to introduction of the endoprosthetic, it can be applied or coated onto the endoprosthetic surface, and/or the inner surface of the bone prior to implantation as will become apparent from the disclosure.

Figure 1:
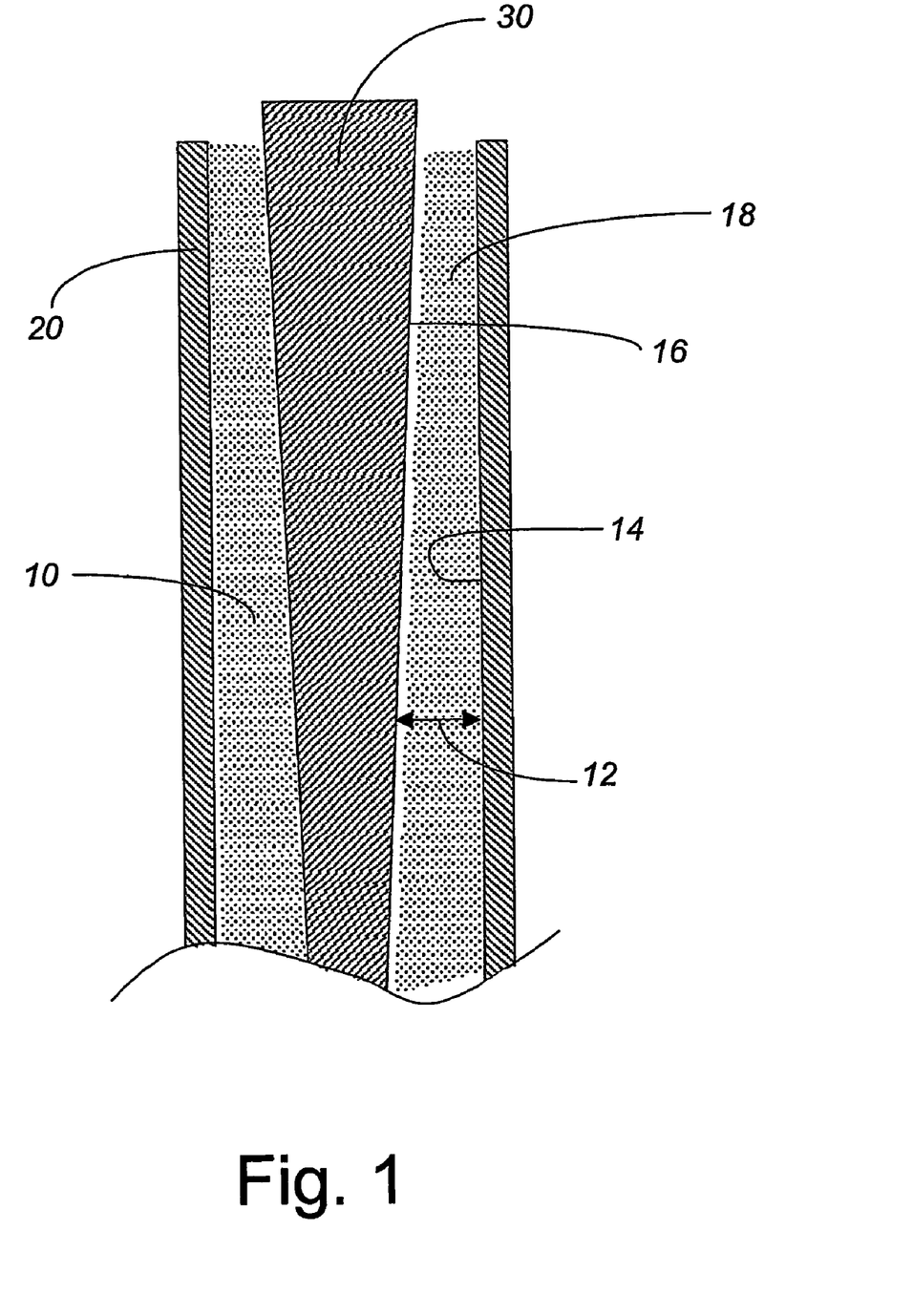
FIG. 1 shows, diagrammatically, a longitudinal cross-section of a long bone having an endoprosthetic implant therein, as well as a compliant barrier layer made from the bone healing composition according to the invention.

Referring to FIG. 1, the bone primer composition provides or results in a compliant barrier layer 10 in the intra-medullary gap 12 between the medullary canal wall 14 and an endoprosthetic surface 16. The medullary gap 12 is shown exaggerated for ease of visualization.

In a preferred embodiment, the inventive composition comprises at least 40, preferably at least 50 or 60, weight percent (dry basis) of a bone endogenous material. The composition also includes an effective amount of a degradable polymer material sufficient to produce a second order porosity in the compliant barrier layer 10 upon degradation (explained below), and a quantify of trophic factors, such as growth factors, in an effective amount to induce osteoblast migration and promote osteointegration of the endoprosthetic implant (also explained below).

The bone endogenous material can be or include any material that is normally found in healthy human bone tissue as biologically occurring molecules. The bone endogenous material can be naturally occurring (for example harvested from a patient) or synthetically prepared via conventional techniques. In particular, the bone endogenous material used in the bone primer composition of the present invention can be or include fibronectin, collagen, laminin, tenascin, proteoglycans, glycosaminoglycans, fibrinogen, hyaluronic acid, elastin, tricalcium phosphate, hydroxyapatite, as well as other extracellular bone matrix materials. The bone endogenous material can also be or include other naturally derived materials such as alginates, vitrogens, vitronectins, and chitosans. The endogenous material can also be a mixture of any of the above materials.

The degradable polymer material can be or include any natural or synthetic degradable polymer that is non- or substantially non-immunogenic. Preferably, the degradable polymer material has a half-life for degradation of 1-60 days, preferably 1-30 days, preferably 1-20 days, preferably 1-14 days, preferably 1-7 days. Suitable degradable polymers include polylactic acid (PLA), polyglycolic acid (PGA), polyanhydrides, polyvinyl alcohol (PVA), poly [L-lactic acid] (PLLA), poly [D,L-lactic acid] (PDLLA) and poly (lactide-co-glycolide) copolymer (PLGA). Alternatively, the degradable polymer material can be or include naturally biologically occurring polymeric species such as chitosan, agarose and alginate.

Growth factors for use in the present invention include BMP-7, BMP-4, PDGF-BB, TGF-β1, tetracycline, bFGF, VEGF, PTH, and PTH-rp. Mixtures of the above can also be used. The growth factors can be in globular protein form or active peptide fragments that promote bone regeneration. There are several distinct advantages of the peptide form. In the peptide form, the factors lack immunogenicity. In addition, small peptide molecules are readily diffusible, and exhibit less promiscuity (i.e. greater specificity) because they can be designed for specificity via conventional techniques. The globular protein form also has several distinct advantages, including tertiary structure, enhanced conformation, and slower rate of uptake and potentially of metabolism.

Preferably, the bone primer composition can also be provided with medicaments, such as antibiotics and/or analgesics. Also preferably, the bone primer composition can be provided with other osteogenic and/or angiogenic nutrients, e.g. glucose, amino acids, glucosamines, etc.

The invented bone primer composition preferably has two material phases; a flow phase and a congealed or semi-solid phase. By flow phase, it is meant that the composition is generally a liquid, preferably a viscous liquid having a viscosity of at least 1, preferably at least 10, preferably at least 100, preferably at least 300, preferably at least 500, preferably at least 700, preferably at least 800, preferably at least 900, preferably at least 1000, cP at 25° C. Such a composition is easily applied within the medullary canal by a surgeon during or prior to implantation of an endoprosthetic device 30. Also, high viscosity minimizes or substantially eliminates air bubble entrainment within the composition as it is poured or delivered into the medullary canal. By congealed phase, it is meant that the composition exists in a solid or pseudosolid or semi-solid material, e.g. a gelatinous material, that no longer flows but is substantially fixed in its dried or congealed form.

Preferably, the bone primer composition is applied within the medullary canal 18 during or prior to endoprosthesis implantation. The procedure is generally as follows. First, the bone 20 that is to receive the endoprosthetic implant 30 is prepped in a conventional manner. Typically, preparation includes resection of the bone end, for example in knee replacement, or femoral/humeral head resection for hip/elbow replacement, followed by the widening and/or reaming of the medullary canal 18 within the bone 20.

Second, a quantity of the invented bone primer composition, in the flow phase, is applied or introduced within the reamed medullary canal 18 by conventional cementing techniques until the composition fills or substantially fills the canal 20. Preferably, the composition is provided in the medullary canal 18 prior to insertion of the endoprosthesis therein. Third, the endoprosthesis is inserted in a conventional manner. It will be understood that insertion of the prosthesis into the medullary canal 20 will result in extrusion of excess bone primer composition up to the excluded volume of the endoprosthesis 30 in the medullary canal. In this manner, the bone primer composition completely fills the intramedullary gap 12 between the implanted prosthesis 30 and the surrounding medullary canal wall 14, minimizing entrained air bubbles. As stated above, the composition is preferably in the flow phase when it is provided (e.g. by pouring, via a syringe, or extrusion through a tube opening) in the medullary canal.

Once the medullary canal is completely (or substantially completely) filled with the invented bone primer composition, the endoprosthesis 30 is inserted in a conventional manner as explained above, and excess or extruded bone primer composition is wiped away.

Following endoprosthesis insertion, the bone primer composition in the intra-medullary gap 12 between the prosthesis and the medullary canal wall 14 preferably undergoes a phase transformation (e.g. sets or polymerizes), into the congealed phase. In the congealed phase, the bone primer composition provides the compliant barrier layer 10 in the medullary gap 12 as shown in FIG. 1, substantially filling the intra-medullary gap 12. The barrier layer 10 preferably completely or substantially completely encapsulates the implanted endoprosthesis 30.

The compliant barrier layer 10 is also preferably porous, preferably having a dual mode porosity that imbibes or is effective to imbibe interstitial fluid from surrounding tissue. Dual mode porosity means that the compliant barrier layer made from the invented bone primer composition in the congealed phase has a first order porosity to accommodate or promote molecular diffusion between the medullary canal wall 14 and the endoprosthetic surface 16, as well as to promote bulk fluid flow or fluid imbibement therebetween, and a second order porosity that provides a pathway through which osteoblasts can enter the medullary gap 12 without the requirement of prior osteoclastic resorption. Preferably, the first order porosity has a first order radial porosity gradient with first order porosity increasing in a radially inward direction from the medullary canal wall 14 to the endoprosthetic surface 16, e.g. with the first order mean Stokes pore diameter increasing from approximately $0.1$-$20 \times 10^{-10}$, preferably $0.5$-$15 \times 10^{-10}$, preferably $1$-$10 \times 10^{10}$, preferably $2$-$8 \times 10^{10}$, preferably $3$-$7 \times 10^{-10}$, preferably $4$-$6 \times 10^{-10}$, preferably about $4$-$5 \times 10^{-10}$, meters adjacent the medullary canal wall 14, to $50$-$300 \times 10^{-10}$, preferably $60$-$250 \times 10^{-10}$, preferably $70$-$200 \times 10^{-10}$, preferably $80$-$150 \times 10^{-10}$, preferably $90$-$120 \times 10^{-10}$, preferably about $100 \times 10^{-10}$, meters adjacent the endoprosthetic surface 16. Preferably, for the first order porosity, the pore size adjacent the canal wall 14 is sufficient to accommodate 300-400 Da molecular weight species, and the pore size adjacent the prosthesis wall 16 is sufficient to accommodate species having greater than 40 kDa molecular weight. Alternatively, the first order radial porosity gradient can be provided as a pore density gradient with increasing pore density toward the implant surface 16. This serves to promote imbibement from the natural bone tissue at the canal wall 14 toward the implant surface 16.

It has been found that the above-described radial first order porosity gradient can be induced by providing a radial temperature gradient during phase transformation from the flow phase to the congealed phase. By heating the prosthesis, e.g. to 40° C., prior to insertion in the medullary canal filled with the bone primer composition, a radial temperature gradient is induced in the surrounding composition. The magnitude and direction of the porosity gradient can be controlled as a function of the magnitude and direction of the temperature gradient. The direction of the temperature gradient can be controlled by either heating or cooling the prosthesis relative to the canal wall 14 prior to insertion. Alternatively, either the canal wall 14 or the prosthesis surface 16 can be coated with a cross-linking agent to promote increased cross-linking of the bone primer composition adjacent that surface, thereby decreasing the porosity of the barrier layer 10 adjacent that surface. The slope of the first order porosity gradient can be controlled by selecting cross-linking agents with suitable kinetics and rate of diffusion in the bone primer composition. In a further alternative embodiment, the porosity gradient can be provided by taking advantage of thixotropic properties of the bone primer composition (differential in shear stress during application produces differences in pore size distribution), or of the different electrochemical properties of the bone and the prosthesis.

The second order porosity preferably comprises a tortuous network of relatively large-pore passages compared to the first order porosity, i.e. preferably having a mean Stokes diameter on the order of $10^{-6}$ meters. The second order porosity in the invented compliant barrier layer 10 provides a tunnel network for the mobilization of osteoblasts from the medullary canal wall 14 through the barrier layer 10 toward the endoprosthetic surface 16. By providing the second order porosity, the osteoclastic resorption step that typically must precede osteoblastic bone synthesis in the ordinary biological process of bone remodeling is preferably reduced or diminished, more preferably substantially eliminated. The result is the minimization of bone consumption or resorption mechanisms (i.e. osteoclastic resorption) and the maximization of bone synthesis mechanisms. In addition, the second order porosity provides a pathway for angiogenic species (such as angiogenesis-stimulating growth factors) and the synthesis of blood flow pathways to osteoblastic synthesis sites. Simultaneously, the first order porosity promotes molecular diffusion of nutrient species required by the osteoblasts in order to synthesize new bone, preferably from the bone endogenous material present in the barrier layer 10. As stated above, the bone primer composition (and therefore the resulting compliant barrier layer 10) preferably comprises, or is made substantially from, a bone endogenous material. As a result, osteoblasts can synthesize new bone directly from the barrier layer material, resulting in the fusion of the surrounding bone to the implanted endoprosthesis 30.

This feature of the present invention represents a significant advance over the prior art. In uncemented arthroplasty, a press fit is achieved between the bone and the prosthesis leaving a gap of up to approximately 2 mm between the implant surface and bone. Alternatively, in the conventional cemented arthroplasty procedure, a bone cement such as polymethyl methacrylate (PMMA) is used to cement an endoprosthesis within a reamed medullary canal, with the reamed canal typically being provided with a slightly smaller diameter than the prosthesis resulting in an interference fit. The interference fit is to ensure intimate contact with the methacrylate cement for both the prosthetic surface and the canal wall. In this conventional technique, bone from the canal wall is not induced to grow toward the implant, or to fill in imperfections or gaps between the prosthesis and the canal wall. In fact, the methacrylate cement layer between the canal wall and the prosthesis is a barrier to the transduction of biological species responsible for generating new bone, such as osteoblasts and osteoblastic nutrients.

Conversely, the present invention provides a compliant barrier layer 10 between the endoprosthetic surface and the canal wall that is substantially made from bone endogenous material, and has the dual mode porosity system described above. The dual mode porosity system permits and actually affirmatively promotes or induces osteoconduction from the canal wall 14 toward (and to) the endoprosthetic surface 16, using the barrier layer 10 itself as the raw material for bone synthesis. Thus, it can be seen that in addition to providing a means of fixing the prosthesis in place, the barrier layer 10 of the present invention effectively promotes osteoconduction via the body's own natural osteogenic mechanism, provides pathways for osteoblastic migration via the second order porosity, and provides pathways for nutrient and growth factor migration via diffusion and convection through the first order porosity. Ultimately, the entire barrier layer 10 is essentially converted to new bone via the body's own osteogenic mechanism, resulting in an effective osteointegration of the endoprosthetic implant within the surrounding bone. In other words, once all of the bone endogenous material in the barrier layer 10 has been used by osteoblasts to synthesize new bone, the end result is a continuous living bone that has grown inward toward and the implant which has now been effectively integrated within the bone, without no or substantially no presence of any interfacial barrier layer remaining between the bone and the implant. This result has never before been possible because the interfacial cement layers of the prior art made true osteointegration of endoprostheses (bone growth all the way up to the implant) impossible.

An additional advantage over conventional bone cements is that the invented barrier layer is a compliant layer, and is less prone to stress fracturing or failure from shearing forces under heavy or impact loading. It is important that the barrier layer 10 is compliant because osteoblastic bone synthesis (osteogenesis) will not occur immediately. It is thus highly desirable to provide a shock-absorbing or "damping" medium between the endoprosthesis 30 and the surrounding bone 20 prior to complete osteoconversion of the barrier layer 10 via osteogenesis. This ensures that the endoprosthesis will not loosen or become unstable in the interim due to stress concentration effects (e.g. through abrupt changes in mechanical properties at the implant-bone interface) or micromotion at the implant-bone interface. The compliant barrier layer 10 also ensures that interstitial fluid containing nutrients and growth/angiogenic factors is pumped between the implant surface and bone (e.g. like compressing and releasing a fluid-filled sponge), and that there is adequate bone-endogenous material in situ for the synthesis of new bone to completely fill the intra-medullary gap 12. Preferably, the compliant barrier layer 10 exhibits strains of 0.01-2.0, preferably 0.01-1.8, preferably 0.01-1.6, preferably 0.01-1.4, preferably 0.01-1.2, preferably 0.01-1.0, preferably 0.01-0.8, preferably 0.01-0.6, preferably 0.015-0.4, preferably about 0.02-0.2% during normal physiologic loading, e.g. from walking.

The mechanism by which the dual mode porosity is believed to promote osteoconduction and conversion of the barrier layer 10 will now be described. The first order porosity gradient as described above promotes mechanical loading-induced mass transport of nutrient species (e.g. glucose, amino acids, oxygen, etc.) required for osteoblastic and angiogenesis metabolism from the medullary canal wall 14 toward the endoprosthetic surface 16. Specifically, the mechanical loading of a bone (e.g. a bone having an endoprosthesis implanted therein) induces bulk fluid flow as well as molecular diffusion or convective perfusion of diffusive species through the bone's pore structure. This property of bone is generally known in the art, and is described, e.g. in the following publications, all of which are incorporated herein by reference:

Knothe Tate, M. L., Niederer, P., and Knothe, U., "In Vivo Tracer Transport Through the Lacunocanalicular System of Rat Bone in an Environment Devoid of Mechanical Loading", Bone, Vol. 22, No. 2, pp. 107-117, February 1998;

Knothe Tate, M. L., Knothe, U., and Niederer, P., "Experimental Elucidation of Mechanical Load-Influenced Fluid Flow and Its Potential Role in Bone Metabolism and Functional Adaptation", Am. J. Med. Sci., Vol. 316, No. 3, pp. 189-195, September 1998;

Knothe Tate, M. L., and Knothe, U., "An ex vivo model to study transport processes and fluid flow in loaded bone", J. Biomech., Vol. 33, pp. 247-254, 2000;

Knothe Tate, M. L., Steck, R., Forwood, M. R., and Niederer, P., "In Vivo Demonstration of Load-Induced Fluid Flow in the Rat Tibia and Its Positional Implications for Processes Associated with Functional Adaptation", J. Exp. Biol., Vol. 203, pp. 2737-2745, 2000; and Knothe Tate, M. L., "Interstitial Fluid Flow", Chapter 22, (pp. 22-1-22-29) *Bone Mechanics Handbook*, Cowin, Stephen C., Ed., CRC Press, New York, 2001.

In addition, without wishing to be bound by a particular theory, it is believed that fluid flow in bone proceeds by one or several of the mechanisms outlined in the paper entitled "*Whither Flows the Fluid in Bone?*" An Osteocyte's Perspective, by Melissa Knothe Tate, Ph.D., contained in U.S. Provisional Patent Application Ser. No. 60/358,160 filed Feb. 20, 2002, incorporated by reference hereinabove.

The inventive composition is prepared initially as an aqueous mixture, e.g., a slurry, suspension, hydrogel, or any other suitable form of aqueous composition. The bone endogenous material is supplied as a powder and suspended via conventional techniques to provide the aqueous mixture. Preferably, this mixture has a viscosity of at least 100 cP or 1000 cP. In a preferred embodiment, the degradable polymer material mentioned above (to provide the second order porosity) is added to the mixture and is admixed to substantially uniformly distribute the degradable polymer throughout the mixture. Upon congealing or setting from the flow phase to the congealed phase, the rapidly degrading polymer rapidly degrades leaving a tortuous network of tunnels or pores throughout the compliant barrier layer 10 to accommodate bulk fluid flow and migration of large cellular species, e.g. osteoblasts. The amount of degradable polymer that is added to the mixture is selected such that the resulting second order porosity (the tunnels left behind in the barrier layer 10 once the polymer has completely degraded) represents a void fraction of 2-40, preferably about 3-30% relative to the total volume of the barrier layer 10 based on said second order porosity. The degradable polymer material is preferably supplied in the form of microspheres or small particulates whose particle size is selected to correspond to the desired pore-size diameter for the second order porosity tunnel network.

This rapidly degrading polymer can be (and preferably is) formulated to include chemical species that are found naturally within osteoclastic resorption lacunae, e.g. TRAP (tartrate resistant acid phosphatase). Such chemical species are left behind within the tortuous pore network following polymeric degradation, where they promote and help direct osteoblastic synthesis of new bone. The second order porosity is important to provide a migratory network for osteoblasts, in order that osteoclasts are not necessary to consume bone or bone primer material in order for the osteoblasts to travel through the barrier layer 10 and to reach the endoprosthetic surface 16. As stated above, the degradable polymer preferably has a half-life of 1-60 days, more preferably about 1-7 days. In general, the shorter the polymer half-life the better, (e.g., it can be less than 1 day) so long as it does not substantially degrade before a surgical implant procedure can be completed. A half-life of 1 day is believed to be long enough to prevent any complications resulting from too rapid polymer degradation. Too long a half-life, e.g. greater than 60 days, and one risks the body's own bone remodeling mechanism will introduce osteoclasts to provide tunnels through the barrier layer 10 via osteoclastic resorption to provide pathways for the osteoblasts.

Alternatively to the degradable polymer, the second order porosity can be provided in the compliant barrier layer 10 via conventional leaching techniques. For example, a leachable particulate species, e.g. a salt compound, can be provided in the bone primer composition mixture in place of the degradable polymer. The salt compound (such as NaCl) is then leached out via conventional techniques such as osmosis leaving behind the tortuous second order porosity network. Leaching methods and leachable species are well known in the art, and any suitable conventional leaching method or species could be used.

The trophic (growth) factors are also provided in the mixture in conventional amounts which are known or ascertainable to a person of ordinary skill in the art based on the present disclosure, such that an effective amount of growth factors is provided to promote osteogenesis as soon as possible after the composition congeals to provide the barrier layer 10 as described above.

In a preferred embodiment, the growth factors are provided by covalently linking the factors to polyethylene glycol (PEG) chains. PEG is a flexible hydrophilic polymer. The growth factor-linked PEG species are then incorporated into the mixture and admixed therein. Upon forming the congealed phase, the PEG chains are covalently bonded to the pore surfaces within the first order porosity of the barrier layer scaffold. According to this embodiment, the growth factors are fixed in place in a uniform distribution throughout the scaffold. By fixing the growth factors in this manner via PEG chains, the growth factors cannot diffuse away or become metabolized. The fixed growth factors are available as exposed ligands that can bind surface receptors of approaching osteoblasts in order to promote osteogenesis at the growth factor fixation site. In other words, the uniform, fixed distribution of growth factors throughout the bone endogenous material scaffold of the barrier layer 10 provides a lure for traveling osteoblasts to synthesize bone at the growth factor fixation sites, ensuring substantially complete osteoconversion of the barrier layer into synthesized new bone.

In another preferred embodiment, the growth factors are loaded into the microspheres or particulates of the degradable polymer responsible for providing the second order porosity described above. As the polymer degrades, the growth factors are left behind, initially concentrated within the newly formed second order porosity network of the bone endogenous material scaffold. In this embodiment, the release of the growth factors within the barrier layer 10 is controlled by the rate of degradation (the half life) of the degradable polymer, which in turn limits the rate of growth factor metabolism. A key advantage to this embodiment is that because the growth factors are initially highly concentrated within the second order porosity, they are readily and immediately available to osteoblasts (which travel through the second order porosity network) which use them in osteogenesis. This embodiment may promote more rapid osteogenesis due to the immediate availability of growth factors for chemotaxis and migration of osteoblasts in the second order porosity network.

Preferably, the bone primer composition mixture can also be provided with a medicament, such as an antibiotic or analgesic, to be slowly released following endoprosthetic implantation. Also preferably, the bone primer composition can be provided with other osteogenic and/or angiogenic nutrients, e.g. glucose, amino acids, etc.

Once the aqueous mixture has been prepared, it is delivered to the medullary canal in the flow phase as described above, and the endoprosthesis is inserted. Following endoprosthetic insertion, the composition undergoes a phase transformation from the flow phase to the congealed phase to provide the invented barrier layer 10 and to securely retain the endoprosthesis therein. The phase change mechanism can be designed according to any suitable mechanism for gellation of a flowable phase in vivo, so long as the gellation mechanism is biocompatible. A preferred gellation mechanism is to use a cross-linking agent to cross-link the bone endogenous material molecules to thereby provide the congealed phase. Suitable cross-linking agents include thrombin, NDGA, DOPA, lysyl oxidase, genipin, microwaves, ultraviolet (UV) light, prolyl hydroxylase, and horseradish peroxidase. The cross-linking agent is selected based on the principal bone endogenous material or materials to provide a functionally cross-linked scaffold from the bone endogenous material(s). In a preferred embodiment, the bone primer composition mixture (flow phase) is prepared separately from the cross-linking agent, and each is delivered in the medullary canal so that they first meet and are mixed within the canal. A double-barrel syringe as known in the art can be used for this purpose, such that the bone primer composition and the cross-linking agent are mixed upon elution from the syringe as they are being delivered into the medullary canal.

Following cross-linking in the medullary gap between the canal wall 14 and the endoprosthesis 16, the bone endogenous material forms the structural backbone or scaffold for the compliant barrier layer 10, and has a characteristic material porosity based on the bone endogenous material, the cross-linking agent used and the degree of cross-linking (e.g. 100% cross-linking results in lowest porosity whereas a lesser degree of cross-linking results in higher porosity). The inherent material porosity of the cross-linked bone endogenous material provides the first order porosity described above, through which nutrient and other species, are induced to diffuse through the barrier layer 10 as a result of cyclical loading of the bone. The degree of cross-linking, and therefore the first order porosity, can be tuned or controlled by varying the amount of cross-linking agent used, temperature, pH, as well as other reaction parameters.

Another highly beneficial effect of this cross-linking is that it promotes or increases the initiation of calcification at the endoprosthesis/barrier layer interface. This calcification ultimately results in cross-linked material between synthesized bone and the adjacent prosthetic surface which in turn provides a higher degree of mechanical coupling and stability between the prosthesis and the bone.

In a further preferred embodiment, the bone primer composition mixture is provided with a quantity of osteoblasts and/or pluripotent cells prior to application to a patient's bone, i.e. within the medullary canal of a bone which is to receive an endoprosthesis. In this embodiment, osteoblasts and/or pluripotent cells are preferably taken from the patient, for example from bone marrow aspirate or blood plasma as known in the art. These cells can be separated or purified via conventional techniques, and then combined with the bone primer composition mixture to provide an osteoprogenitor cell-enriched bone primer composition mixture. The enriched composition is thus applied, e.g. within the medullary canal, already having a quantity of osteoblasts and or/pluripotent cells interspersed throughout the composition. Once the composition has congealed, osteoblasts can immediately begin synthesizing new bone from bone endogenous material present in the congealed phase.

The invented bone primer can be used to promote bone synthesis and fusion toward (with) any non-cemented endoprosthetic implant, including joint replacement implants and dental posts. The resulting osteogenesis in the intramedullary gap 18 and bone fusion to the endoprosthetic surface 16 provides an endoprosthesis 30 with a longer useful life. Longer life is due in part to the fact that the prosthesis no longer moves within the medullary canal 18, but rather is stabilized therein shortly following implantation by the compliant barrier layer 10. Further, fusion in-vivo of bone material to the endoprosthetic surface 16 provides lasting stability of the prosthesis within the bone 20.

A further benefit of the invented bone primer composition is that it does not introduce any particulate debris into the medullary canal. Particulate debris, common with conventional bone cements, coated implant surfaces, and structured metallic implant surfaces (e.g. having non-smooth surface topography), has been associated with the onset of osteolysis and subsequent endoprosthetic implant failure.

The invention is not limited to use only for endoprosthetic implantation. The invented bone primer composition can be applied to any bone, anywhere it is desirable to promote bone healing or bone synthesis; e.g. the invented bone primer composition can be applied to fracture fixation (such as fracture healing) in broken bones, or treatment of osteoporotic bone (i.e. to promote osteogenesis and strengthen the bone). The invented bone primer composition is particularly useful to strengthen or repair osteoporotic bone, where there is not a lot of nascent bone material to start with. In this embodiment, the invented bone primer composition promotes accelerated osteogenesis within the osteoporotic bone, thereby strengthening the bone. This can be accomplished with little or no destruction of the osteoporotic bone; e.g. the bone primer composition is simply coated onto the osteoporotic bone, or alternatively, used to fill in defects. In addition, the invented bone primer composition can be used to reconstruct a segmental defect in the case of missing bone, e.g., following tumor resection and/or polytrauma. The invention is particularly useful when applied to or within a spinal cage to enhance spinal fusion via bony ingrowth to the spinal cage.

In general, the invented bone primer composition can be applied anywhere it is desired to promote osteogenesis within or adjacent to bone.

Although the hereinabove described embodiments of the invention constitute the preferred embodiments, it should be understood that modifications can be made thereto without departing from the scope of the invention as set forth in the appended claims.

What is claimed is:

1. A method of promoting osteogenesis comprising the steps of:
    a) providing a composition comprising a bone endogenous material in a flow phase;
    b) applying said composition to a site within a patient where it is desired to synthesize new bone;

c) cross-linking said bone endogenous material at the application site to transform said composition from said flow phase to a congealed phase; and d) providing a dual mode porosity system in said composition in said congealed phase, said congealed phase of said composition having a first order porosity having a mean Stokes pore diameter of $0.1-300\times10^{-10}$ meters and a second order porosity having a mean Stokes pore diameter on the order of $10^{-6}$ meters, said first order porosity being provided in bone endogenous material comprising a material selected from the group consisting of alginates, vitrogens, vitronectins, chitosans, and mixtures thereof.

2. A method of promoting osteogenesis comprising the steps of:

a) providing a composition comprising a bone endogenous material in a flow phase;

b) applying said composition to a site within a patient where it is desired to synthesize new bone;

c) cross-linking said bone endogenous material at the application site to transform said composition from said flow phase to a congealed phase; and d) providing a dual mode porosity system in said composition in said congealed phase, said congealed phase of said composition having a first order porosity having a first mean Stokes pore diameter of $0.1-300\times10^{-10}$ meters and a second order porosity having a second mean Stokes pore diameter on the order of $10^{-6}$ meters, said first order porosity being provided in cross-linked bone endogenous material.

3. A method according to claim 2, said bone endogenous material comprising a material selected from the group consisting of fibronectin, collagen, laminin, tenascin, proteoglycans, glycosaminoglycans, fibrinogen, hyaluronic acid, elastin, tricalcium phosphate, hydroxyapatite, other extracellular bone matrix materials, and mixtures thereof.

4. A method according to claim 2, said composition in said flow phase having a viscosity of at least 1 cP at 25° C.

5. A method according to claim 2, said composition further comprising an osteogenic and/or angiogenic nutrient.

6. A composition according to claim 2, said composition further comprising a quantity of osteoblasts and/or pluripotent cells.

7. A method according to claim 2, said first order porosity being provided as a characteristic material porosity of said bone endogenous material after cross-linking, said first order porosity being determined in part via selection of a cross-linking agent and the degree of cross-linking of said bone endogenous material.

8. A method according to claim 7, said cross-linking agent comprising an agent selected from the group consisting of thrombin, NDGA, DOPA, lysyl oxidase, genipin, microwaves, ultraviolet light, prolyl hydroxylase, horseradish peroxidase, and mixtures thereof.

9. A method according to claim 2, said composition further comprising a degradable polymer material, said degradable polymer material degrading to leave a tortuous network of tunnels or pores in said composition in said congealed phase, said tortuous network of tunnels or pores, resulting from said degradation of said degradable polymer material, forming said second order porosity.

10. A method according to claim 9, said degradable polymer material having a half-life for degradation of 1-60 days.

11. A method according to claim 9, said degradable polymer material having a half-life for degradation of about 1-7 days.

12. A method according to claim 9, said degradable polymer material having a half-life for degradation of less than 1 day.

13. A method according to claim 9, said composition in said congealed phase being provided with a second order void fraction of 2-40% based on said second order porosity.

14. A method according to claim 9, said degradable polymer material being provided in an amount sufficient to result in a second order void fraction of 2-40% based on said second order porosity.

15. A method according to claim 9, said degradable polymer material being provided in the form of microspheres or particulates, said microspheres or particulates having a particle size selected to correspond to a desired pore-size diameter for said second order porosity.

16. A method according to claim 9, said degradable polymer material comprising a material selected from the group consisting of polylactic acid, polyglycolic acid, polyanhydrides, polyvinyl alcohol, poly [L-lactic acid], poly [D,L-lactic acid], and poly (lactide-co-glycolide) copolymer.

17. A method according to claim 9, said degradable polymer material comprising a material selected from the group consisting of chitosan, agarose and alginate.

18. A method according to claim 9, said degradable polymer being formulated to include a chemical species that is found naturally within osteoclastic resorption lacunae, wherein upon said degradation of said degradable polymer, said chemical species is left behind within said second order porosity.

19. A method according to claim 18, said chemical species comprising tartrate resistant acid phosphatase.

20. A method according to claim 2, said second order porosity further providing a pathway for angiogenic species and for the synthesis of blood flow pathways to osteoblastic bone synthesis sites.

21. A method according to claim 2, said composition further comprising a quantity of osteoblasts, said osteoblasts, after said composition has undergone said phase transformation and is in said congealed phase, synthesizing new bone from said bone endogenous material present in said congealed phase.

22. A method according to claim 2, said first order porosity providing a pathway for molecular diffusion of nutrient species required by osteoblasts for osteogenesis, and for bulk fluid flow or fluid imbibement through said composition in said congealed phase, said second order porosity providing a migratory network for osteoblasts through said composition in said congealed phase.

23. A method according to claim 22, further comprising mobilization of osteoblasts through said composition in said congealed phase via said second order porosity.

24. A method according to claim 23, further comprising osteoconverting at least a portion of said bone endogenous material in said composition in said congealed phase into new bone via osteoblastic bone synthesis.

25. A method according to claim 24, further comprising substantially completely converting said bone endogenous material in said congealed composition into new bone.

26. A method according to claim 2, said composition further comprising a medicament.

27. A method according to claim 2, said composition further comprising a quantity of growth factors in an effective amount to promote osteoblastic migration through said composition in the congealed phase.

28. A method according to claim 27, a portion of said growth factors being in globular protein form.

29. A method according to claim 27, a portion of said growth factors being in the form of active peptide fragments.

30. A method according to claim 27, said growth factors being covalently linked to polyethylene glycol chains.

31. A method according to claim 27, said growth factors comprising factors selected from the group consisting of BMP-7, BMP-4, PDGF-BB, TGF-b1, tetracycline, bFGF, VEGF, PTH, and PTH-rp.

32. A method according to claim 27, further comprising covalently linking said growth factors to polyethylene glycol chains, and incorporating said growth factor-linked polyethylene glycol species into said composition in said flow phase, wherein, after said composition is transformed into said congealed phase, the polyethylene glycol chains are covalently bonded to pore surfaces within said first order porosity of said composition in said congealed phase, said growth factors being thereby fixed in place in a substantially uniform distribution throughout said congealed composition.

33. A method according to claim 27, further comprising
a) providing a degradable polymer material, in the form of microspheres or particulates, in said composition, said microspheres or particulates having a particle size selected to correspond to a desired pore-size diameter for said second order porosity;
b) loading said growth factors into said microspheres or particulates of said degradable polymer material;
c) degrading said degradable polymer material, after said composition is transformed into said congealed phase, to leave a tortuous network of tunnels or pores in said composition in said congealed phase, said tortuous network of tunnels or pores, resulting from said degradation of said degradable polymer material, forming said second order porosity;
d) releasing said growth factors as said degradable polymer material degrades, thereby initially concentrating said growth factors within said second order porosity of said composition in said congealed phase, said growth factors being available to osteoblasts migrating through said second order porosity to be used in osteogenesis.

34. A method according to claim 2, said composition being applied to enhance fracture healing of a broken bone.

35. A method according to claim 2, said composition being applied to reconstruct a segmental defect to replace missing bone.

36. A method according to claim 2, further comprising the steps of implanting a spinal cage into said patient's spine, and providing said composition in said spinal cage to enhance spinal fusion.

37. A method according to claim 2, further comprising implanting an endoprosthesis into a medullary canal of a long bone from which the joint has been resected, and providing said composition in an intra-medullary gap between a medullary canal wall of said bone and said endoprosthesis implanted within said medullary canal to provide in said gap a compliant barrier layer composed of said composition in said congealed phase having said dual mode porosity.

38. A method according to claim 37, said first order porosity having a radial porosity gradient in said barrier layer such that said first order porosity increases in a radially inward direction from said medullary canal wall to said endoprosthesis, said first order porosity having a first order mean Stokes pore diameter of about $0.1\text{-}20\times10^{-10}$ meters adjacent said medullary canal wall, and a first order mean Stokes pore diameter of about $50\text{-}300\times10^-$ meters adjacent said endoprosthesis.

39. A method according to claim 37, said second order porosity being provided via degradation of a degradable polymer material, wherein said degradation of said degradable polymer material leaves a tortuous network of tunnels or pores in said compliant barrier layer, said tortuous network of tunnels or pores forming said second order porosity therein.

40. A method according to claim 37, said bone endogenous material comprising a material selected from the group consisting of fibronectin, collagen, laminin, tenascin, proteoglycans, glycosaminoglycans, fibrinogen, hyaluronic acid, elastin, tricalcium phosphate, hydroxyapatite, other extracellular bone matrix materials, and mixtures thereof.

41. A method according to claim 37, said bone endogenous material comprising a material selected from the group consisting of alginates, vitrogens, vitronectins, chitosans, and mixtures thereof.

42. A method according to claim 37, said composition further comprising a quantity of growth factors.

43. A method according to claim 42, said growth factors being selected from the group consisting of BMP-7, BMP-4, PDGF-BB, TGF-b1, tetracycline, bFGF, VEGF, PTH, and PTH-rp.

44. A method according to claim 42, said growth factors being covalently linked to polyethylene glycol chains, said growth factor-linked polyethylene glycol species being covalently bonded to pore surfaces within said first order porosity of said compliant barrier layer, said growth factors being thereby fixed in place in a substantially uniform distribution throughout said compliant barrier layer.

45. A method according to claim 42, said growth factors being initially concentrated within said second order porosity of said compliant barrier layer, said growth factors being available to osteoblasts migrating through said second order porosity to be used in osteogenesis.

46. A method according to claim 37, said compliant barrier layer exhibiting a strain of 0.01-2.0% during normal physiologic loading of said bone.

47. A method according to claim 37, said bone endogenous material being initially present in said compliant barrier layer in an amount of at least 50 weight percent on a dry basis.

48. A method according to claim 2, said composition further comprising a quantity of cells.

49. A method of promoting osteogenesis comprising the steps of:
a) providing a composition comprising a bone endogenous material in a flow phase;
b) applying said composition to a site within a patient where it is desired to synthesize new bone;
c) cross-linking said bone endogenous material at the application site to transform said composition from said flow phase to a congealed phase; and
d) providing a dual mode porosity system in said composition in said congealed phase, said congealed phase of said composition having a first order porosity having a first mean Stokes diameter and a second order porosity having a second mean Stokes diameter, said second mean Stokes diameter being larger than said first mean Stokes diameter;
said first order porosity being provided in cross-linked bone endogenous material;
said second order porosity being provided via a leaching technique, wherein a leachable species is provided to said composition, and is leached out of said composition in said congealed phase leaving behind said second order porosity.

50. A method of promoting osteogenesis comprising the steps of:
a) providing a composition comprising a bone endogenous material in a flow phase;

b) applying a quantity of said composition, in said flow phase, within a medullary canal of a bone to substantially fill said canal with said composition, d) inserting an endoprosthesis in said medullary canal having said composition therein and extruding an excess of said composition from said canal to accommodate the volume of said endoprosthesis in the medullary canal, and e) cross-linking bone endogenous material remaining in the medullary canal to transform the composition in said canal from said flow phase into a congealed phase, thereby forming a barrier layer between the endoprosthesis and a wall of the canal, said congealed phase of said composition having a first order porosity that has a first mean Stokes pore diameter of $0.1\text{-}300\times10^{-10}$ meters and a second order porosity that has a second mean Stokes pore diameter on the order of $10^{-6}$ meters, said first order porosity being provided in cross-linked bone endogenous material.

51. A method according to claim 50, further comprising reaming said medullary canal prior to applying said composition therein.

52. A method according to claim 50, said first order porosity providing a pathway for molecular diffusion of nutrient species required by osteoblasts for osteogenesis, and for bulk fluid flow or fluid imbibement through said barrier layer, said second order porosity providing a migratory network for osteoblasts through said barrier layer without the requirement of prior osteoclastic resorption.

53. A method according to claim 52, further comprising cyclically mechanically loading said bone to enhance molecular transport of nutrient species and growth factors via convection through said first order porosity into said barrier layer, said osteoblasts using said nutrient species and said growth factors to synthesize new bone using said bone endogenous material of said barrier layer as raw material for new bone synthesis.

54. A method according to claim 53, further comprising osteoconverting at least a portion of said bone endogenous material of said barrier layer into new bone via osteoblastic bone synthesis.

55. A method according to claim 54, further comprising substantially completely converting said barrier layer into new bone.

56. A method according to claim 53, said cyclic mechanical loading of said bone stimulating bone cells at the medullary canal wall, and inducing bulk fluid flow through said barrier layer via said second order porosity, thereby stimulating recruitment and activity of osteoblasts in said barrier layer.

57. A method according to claim 53, said cyclic mechanical loading of said bone facilitating diffusion of high-molecular weight factors through said barrier layer, said high-molecular weight factors having a molecular weight greater than 40,000 Da.

58. A method according to claim 50, further comprising mobilization of osteoblasts from the medullary canal wall through the barrier layer toward the endoprosthesis via said second order porosity.

59. A method according to claim 58, osteoclastic resorption being substantially eliminated.

60. A method of promoting osteogenesis comprising the steps of:
a) providing a composition comprising a bone endogenous material in a flow phase;
b) applying a quantity of said composition, in said flow phase, within a medullary canal of a bone to substantially fill said canal with said composition,
d) inserting an endoprosthesis in said medullary canal having said composition therein and extruding an excess of said composition from said canal to accommodate the volume of said endoprosthesis in the medullary canal, and
e) cross-linking bone endogenous material remaining in the medullary canal to transform the composition in said canal from said flow phase into a congealed phase, thereby forming a barrier layer between the endoprosthesis and a wall of the canal, said congealed phase of said composition having a first order porosity that has a first mean Stokes diameter and a second order porosity that has a second mean Stokes diameter, said second mean Stokes diameter being larger than said first mean Stokes diameter,
said first order porosity increasing in an inward direction from the medullary canal wall to the endoprosthesis.

61. A method according to claim 60, said first order porosity having a first order mean Stokes pore diameter of about $0.1\text{-}20\times10^{-10}$ meters adjacent the medullary canal wall, and a first order mean Stokes pore diameter of about $50\text{-}300\times10^{-10}$ meters adjacent the endoprosthesis.

62. A method according to claim 61, further comprising providing a temperature gradient in said composition between said endoprosthesis and said canal wall to induce a magnitude and direction of said radial porosity gradient.

63. A method according to claim 62, said temperature gradient being provided by heating said endoprosthesis prior to insertion in said medullary canal.

64. A method according to claim 61, further comprising coating said canal wall or said endoprosthesis with a cross-linking agent to promote increased cross-linking of said bone endogenous material adjacent said canal wall or said endoprosthesis.

65. A method of promoting osteogenesis comprising the steps of:
a) providing a composition comprising a bone endogenous material in a flow phase;
b) applying a quantity of said composition, in said flow phase, within a medullary canal of a bone to substantially fill said canal with said composition,
d) inserting an endoprosthesis in said medullary canal having said composition therein and extruding an excess of said composition from said canal to accommodate the volume of said endoprosthesis in the medullary canal,
e) coating said canal wall or said endoprosthesis with a cross-linking agent to promote increased cross-linking of said bone endogenous material adjacent said canal wall or said endoprosthesis, and
f) cross-linking bone endogenous material remaining in the medullary canal to transform the composition in said canal from said flow phase into a congealed phase, thereby forming a barrier layer between the endoprosthesis and a wall of the canal,
said congealed phase of said composition having a first order porosity that has a first mean Stokes diameter and a second order porosity that has a second mean Stokes diameter, said second mean Stokes diameter being larger than said first mean Stokes diameter.

* * * * *

UNITED STATES PATENT AND TRADEMARK OFFICE
CERTIFICATE OF CORRECTION

PATENT NO. : 7,879,107 B2  Page 1 of 1
APPLICATION NO. : 10/504652
DATED : February 1, 2011
INVENTOR(S) : Melissa L. Knothe Tate and Ulf R. Knothe It is certified that error appears in the above-identified patent and that said Letters Patent is hereby corrected as shown below:

At Col. 2, Line 34, replace "bone prime" with "bone primer".

At Col. 2, Line 59, replace "quantify" with "quantity".

At Col. 4, Line 52, replace "$1\text{-}10\times 10^{10}$" with "$1\text{-}10\times 10^{-10}$", and replace "$2\text{-}8\times 10^{10}$" with "$2\text{-}8\times 10^{-10}$".

At Col. 6, Line 28, delete the word "and" after the word "toward".

At Col. 6, Line 29, replace "without" with the word "with".

In Claim 38 at Col. 13, Line 64, replace "$50\text{-}300\times 10^{-}$" with "$50\text{-}300\times 10^{-10}$".

Signed and Sealed this
Third Day of May, 2011

David J. Kappos
*Director of the United States Patent and Trademark Office*